United States Patent [19]

Ogita

[11] Patent Number: 4,744,952
[45] Date of Patent: May 17, 1988

[54] TEST PAPER FOR DETERMINING THE CONCENTRATION OF HALOGEN IONS BY FILTER PAPER CHROMATOGRAPHY, AND MANUFACTURING PROCESS FOR AND USE OF THE SAME

[76] Inventor: Zen-ichi Ogita, No. 2556-4-1-102, Suehiro-Cho, Gofuku, Toyama-Shi, Toyama-Ken, Japan

[21] Appl. No.: 829,110

[22] Filed: Feb. 14, 1986

[30] Foreign Application Priority Data

Feb. 22, 1985 [JP] Japan .................................. 60-34998

[51] Int. Cl.[4] ...................... G01N 30/90; G01N 31/22
[52] U.S. Cl. ........................................ 422/56; 422/70; 436/124; 436/162
[58] Field of Search ............................. 422/70, 56, 58; 436/162, 56, 57, 124, 125; 427/2; 162/162, 164.5, 165

[56] References Cited

U.S. PATENT DOCUMENTS

| | | |
|---|---|---|
| 1,913,283 | 6/1933 | McCormick et al. ........ 162/164.5 X |
| 2,676,874 | 4/1954 | Berchmans ...................... 422/56 X |
| 3,420,205 | 1/1969 | Morison .......................... 422/56 X |
| 3,447,904 | 6/1969 | Rupe . |
| 3,510,263 | 5/1970 | Hach ............................... 422/56 X |
| 4,094,647 | 6/1978 | Deutsch et al. .................... 422/56 |
| 4,211,532 | 7/1980 | Tobari et al. . |

FOREIGN PATENT DOCUMENTS

0044348 3/1983 Japan .................................. 436/162

OTHER PUBLICATIONS

The Merck Index, Tenth Edition, Merck & Co., Inc., Rahway, N.J., 1983, p. 165.
Touchstone et al., "Practice of Thin Layer Chromatography", 2nd Edition, John Wiley & Sons Inc., New York, 1983, pp. 10, 11, 270 and 271.

Primary Examiner—Barry S. Richman
Assistant Examiner—Jill Johnston
Attorney, Agent, or Firm—Parkhurst & Oliff

[57] ABSTRACT

A test paper which is disclosed herein comprises a filter paper bearing a mixed berberine sulfate/pigment solution applied on a part thereof. The mixed berberine sulfate/pigment solution is produced by dissolving berberine sulfate and a pigment in a solvent such as water or an organic solvent. The test paper is used to determine the concentration of common salt in an aqueous common salt containing solution of urine or food as well as the content of chlorine or other halogen ions such as bromine and iodine ions in an aqueous halogen-containing solution. The test paper may be made by dissolving a berberine sulfate and a pigment in a solvent and applying the resulting mixed berberine/pigment solution onto a portion of a filter paper. The pigment may be Patent Blue V.

5 Claims, 2 Drawing Sheets

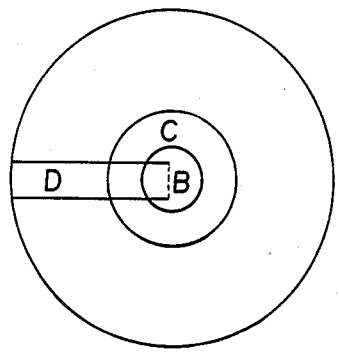
FIG. 2
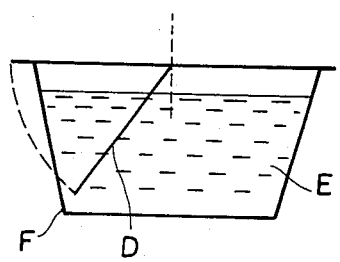
FIG. 4
FIG. 3
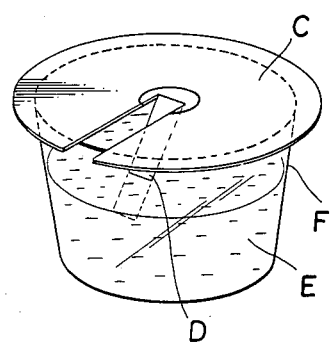

TEST PAPER FOR DETERMINING THE CONCENTRATION OF HALOGEN IONS BY FILTER PAPER CHROMATOGRAPHY, AND MANUFACTURING PROCESS FOR AND USE OF THE SAME

BACKGROUND OF THE INVENTION

The present invention relates to a test paper for use in the determintion of the concentration of common salt contained in urine and food for the purpose of personal health management, as well as the content of halogen ions such as bromine and iodine ions contained in water or soil for the inspection thereof, and further to a process for manufacturing such a paper and the use of the same.

Most of methods for determining the content of a halogen ion such as chloride ion, which are conventionally known, use silver or mercuric nitrate solution, and involves subjecting the silver or mercuric nitrate solution to the reaction with a sample of halogen-containing solution to produce water-insoluble silver or mercuric chloride. Recently, a chloride meter has been developed as a simple measuring instrument utilizing a coulometric titration. However, the conventional determining methods utilizing the precipitation of metal chlorides are accompanied by a problem in environmental pollution because of the toxicity of metal ions employed such as silver, mercury and the like. In addition, the conventional methods utilizing a coulometric titration require an expensive apparatus and hence, are generally not suitable.

SUMMARY OF THE INVENTION

It is known that berberine is one of the alkaloids having a chemical structure of quanternary amine and is soluble in water and alcohols, but berberine chloride or another halide produced from the reaction of berberine with chlorine ion or another halogen ion such as bromine or iodine ion is in the form of a yellow crystal and extremely difficult to be solubilized in water.

The present inventor has made attempts to develop a method for qualitatively and quantitatively determining the content of chlorine ion as well as other halogen ions utilizing the properties of berberine chloride and other halides in that they are extremely difficult to be solubilized in water and consequently has discovered that when berberine sulfate is developed with water as a solvent in a filter paper chromatography, a tailing occurs due to extremely small amounts of the components contained in the filter paper, resulting in the impossibility of correctly determining Rf value of the berberine, but the maximum flow distance within a given range is proportional to the quantity of the berberine. Thus, the present invention has been accomplished primarily on the basis of such an interest phenomenon and the fact that the produced berberine halides which are difficult to solubilize in water remain at the placing points, while unreacted berberine flows to a spot corresponding to the content thereof.

Further, another factor leading to the accomplishment of the present invention is in that a coloring matter or pigment could be found which is not bonded to berberine and berberine halides and has a stable Rf value slightly greater than the maximum value of flow distance of the berberine.

It is therefore an object of the present invention to provide a test paper for use in the determination of the content of a halogen ion, which enables the concentration of common salt contained in urine or food as well as the content of halogen ions such as bromine and iodine ions contained in water or soil to be determined within a reduced time and in a correct and simple manner.

It is another object of the present invention to provide such a test paper which utilizes a filter paper chromatography instead of a merely dipping and reading method conventionally employed.

It is further object of the present invention to provide a process for making such a test paper.

It is still further object of the present invention to provide a method for determining the concentration of common salt contained in an aqueous solution of urine or food, as well as the content of halogen ions such as bromine and iodine ions contained in water or soil by use of such a test paper.

According to the present invention, the above objects are accomplished by providing a test paper comprising a filter paper bearing a mixed berberine sulfate/pigment solution applied on a part thereof, the mixed solution being produced by dissolving berberine sulfate and a pigment in water or an organic solvent such as alcohols including methanol and acetone, so that the concentration of salts contained in urine or food as well as the content of halogen ions such as bromine and iodine ions contained in water or soil can be determined by a partial affinity filter paper chromatography with the aqueous urine or food solution or halogen ion-containing aqueous solution used as a developer solvent.

The pigment contained in the mixed berberine sulfate/pigment solution of the present invention has an Rf value greater than that of berberine in filter paper chromatography for urine, an aqueous common salt-containing solution or an aqueous halogen ion-contianing solution, with said solution being used as a developing solution. In addition, the pigment does not react with halogen ions.

In addition, according to the present invention, there is provided a process for manufacturing a test paper for use in the determination of the concentration of common salt contained in urine or food as well as the content of halogen ions such as bromine and iodine ions contained in water or soil determined by a partial affinity filter paper chromatography with the aqueous urine or food solution or halogen ion-containing aqueous solution used as a developer solvent, which comprises the steps of dissolving berberine sulfate and a pigment in water or an organic solvent such as alcohols including methanol and acetone, and applying the resulting mixed berberine sulfate/pigment solution on a portion of a filter paper.

Further, according to the present invention, there is provided a method for determining, with such a test paper as described above, the concentration of common salt contained in urine or food as well as the content of halogen ions such as bromine and iodine ions contained in water or soil determined by a partial affinity filter paper chromatography with the aqueous urine or food solution or halogen ion-containing aqueous solution used as a developer solvent.

With such a test paper, the determination may be achieved by dipping it in an aqueous solution containing chlorine, bromine or/and iodine ion(s) to conduct a partial affinity filter paper chromatography, so that the content of halogen ion(s) can be presumed from the chromatogram.

Any of the conventional quantitative determinations using a test paper have employed a dipping and reading method. On the other hand, it has been confirmed that a partial affinity filter chromatographic determining method according to the present invention is excellent as a simple quantitative determination process, as compared with the prior art.

Therefore, the concentration of common salt contained in urine or food as well as the content of halogen ions such as bromine and iodine contained in water or soil can be determined within a reduced time with an exactness which has been not found in the prior art and in a simple manner by a partial affinity filter paper chromatography with the aqueous urine or food solution or halogen ion-containing aqueous solution used as a developer solvent.

BRIEF DESCRIPTION OF THE DRAWINGS

The above and other objects, features and advantages of the present invention will become apparent from a reading of the following description of preferred embodiments taken in conjunction with the accompanying drawings in which:

FIG. 2 is a diagram for illustrating a test paper according to the present invention for use in circular filter paper chromatography and how to presume the concentration of salt, wherein the character B denotes a region in which a mixed berberine sulfate/pigment solution is applied in an amount of 5 μl; and FIG. 3 is perspective view of FIG. 2; and FIG. 4 is a longitudinal sectional view of FIG. 3.

DETAILED DESCRIPTION OF THE PREFERRED EMBODIMENTS

Figure 1:
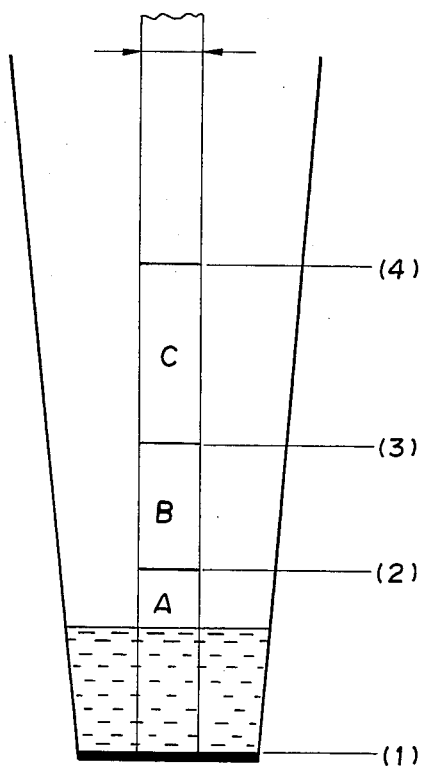
FIG. 1 is a diagram illustrating a test paper according to the present invention for use in rising type filter paper chromatography and how to presume the content of a halogen ion in the resulting chromatogram, wherein the character B designates the region in which a mixed berberine sulfate/pigment solution is applied in an amount of 5 μl.

Patent Blue V is one of the pigments which are not bonded to berberine and berberine halides and have a stable Rf value slightly greater than the maximum valaue of flow rate of the berberine, as described above. The present invention contemplates a test paper made through the application of a green mixed Patent Blue V/berberine sulfate solution on a portion of a filter paper. The test paper may be in the form of a rectangular or circular filter paper. In determining the concentration of common salt in urine or an aqueous common salt-containing solution as well as the content of a halogen ion in an aqueous halogen ion-containing solution, the test paper is subjected to a chromatography for such aqueous solution in a rising or falling manner with the aqueous solution used as a developing solvent. Thereupon, the berberine reacts with chlorine ion as well as another halogen ion to form berberine chloride or another halide difficult to be solubilized in water, by an amount corresponding to the content of chlorine ion or another halogen ion, and only the unreacted remaining free berberine develops on the test paper, while the yellow spot of the berberine chloride or another halide does not substantially develop from the placing point, thus providing a partial affinity filter paper chromatogram. The area of the yellow spot makes it possible to presume the concentration of common salt. In addition, the separation between the blue Patent Blue V and the yellow berberine also enables the presumption of the content of chlorine ion or another halogen ion. More specifically, because the quantity of the free berberine decreases depending on the content of halogen ion, the flow distance of the whole of berberine is reduced, but the Patent Blue V normally flows. Therefore, the blue portion of the pigment is gradually separated away from the green portion formed of the yellow and blue portions in the mixed solution, and the berberine halide remains as a yellow spot.

In this manner, the content of chlorine or another halogen ion contained can be easily decided from the resulting chromatogram. It is to be understood that the sensitivity in the quantitative analysis of chlorine, bromine or iodine ion by use of the test paper according to the present invention can be governed by adjusting the amount of berberine sulfate in the mixed solution.

For the production of a test paper according to the present invention, berberine sulfate and a pigment may be dissolved in a solvent to form a mixed berberine sulfate/pigment solution. Such solvents which may be used include water and organic solvents such as alcohols, e.g., methanol, and acetone. Then, the mixed solution is applied on a portion of a filter paper to provide a test paper.

The amount of berberine sulfate used may be in a range of 5 to 25 mg per milliliter of the mixed solution. The amount of pigment, Patent Blue V used may be in a range of 0.2 to 0.5 mg per milliliter of the mixed solution.

The filter paper which may be used may be hard and contain little fiber and further, may have a uniform wettability. In addition, the filter paper may be rectangular or circular.

The present invention will now be further described by way of Examples which are intended to illustrate and not intended to limit the present invention.

EXAMPLE 1

(Production of Test Paper)

2.5 g of berberine sulfate and 20 mg of Patent Blue V were dissolved in 100 ml of methanol to produce a green mixed berberine sulfate/Patent Blue V solution. Then, the mixed solution was applied in an amount of 5 μl on a filter paper in a region B ($10 \times 5$ mm$^2$) as shown in FIG. 1 (use of filter paper No. 27 or No. 1650 available form TOYO ROSHI CO., LTD., in Japan) to provide a test paper.

EXAMPLE 2

(Production of Test Paper)

2.5 g of berberine sulfate and 25 mg of Patent Blue V were dissolved in 100 ml of methanol to produce a green mixed berberine sulfate/Patent Blue V solution. Then, the mixed solution was applied in an amount of 5 μl on a circular filter paper (No. 5 C available from TOYO ROSHI CO., LTD., in Japan) in a circular region B drawn with a radius of 5 mm at the center of the filter paper to provide a test paper.

EXAMPLE 3

(Determination of Concentration of Common Salt)

(1) Rising Chromatography Using 5 mm Wide Filter Paper Strip (see FIG. 1)

Standard solutions containing sodium chloride dissolved respectively in an amount of 20, 18, 16, 12, 10, 8 and 6 g/liter therein are placed in an amount of 25 ml into a 200 ml cup for urine inspection, respectively (in this case, the height from the bottom of the cup; about 10 mm). One end of the test paper obtained in Example 1 is dipped in each standard solution and developed for a period of 1 to 3 minutes.

With the standard solution of 20 g/l common salt, the blue portion of Patent Blue V starts to separate within 1 minute. When the leading end of the green mixed solution developed with deionized water free of common salt reaches a point shown at 4 in FIG. 1 (in about 3 minutes), the filter paper strip is pulled up out of the standard solution, and water is wiped with a filter paper to stop the development. The resulting chromatogram is used to make a standard diagram. In the actual determination, the previously made standard diagram enables the content of common salt to be presumed from the length of the blue portion of Patent Blue V in a region C, as well as the length of the yellow portion of berberine halide in a region B or the length of the green portion between blue portion (Patent Blue V) and yellow portion (berberine halide).

(2) Circular Filter Paper Chromatography (see FIG. 2)

A notch is made in the test filter paper obtained in Example 2 to extend from the periphery to the center of the filter paper with a width of 5 mm (region D). The portion D is used for absorbing up the solvent by being folded to back surface. Urine or common salt-containing aqueous solution is placed in an amount of 25 ml into a developing solvent cup F. The circular filter paper is placed horizontally on the cup, dipping the portion D in the solvent. The resulting cup is left to stand in a hermetrically sealed vessel for a period of 3 to 5 minutes. When the leading end of the solvent occupies the circular region B having a radius of 10 mm, the filter paper is removed out of the vessel, and water is wiped off with a filter to stop the development. The separated image is compared with the previously made diagram to decide the content of common salt.

What is claimed is:

1. A test paper for determining the concentration of halogen ions in a solution by filter paper chromatography, said test paper comprising a filter paper having a portion coated with a mixed berberine sulfate/Patent Blue V solution, said mixed berberine sulfate/Patent Blue V solution being produced by dissolving berberine sulfate and Patent Blue V in water or an organic solvent.

2. A test paper according to claim 1, wherein said mixed berberine sulfate/Patent Blue V solution is produced by dissolving berberine sulfate and Patent Blue V in an organic solvent and said organic solvent is selected from the group consisting of alcohols and acetone.

3. A test paper according to claim 1, wherein the concentration of said berberine sulfate contained in said mixed berberine sulfate/Patent Blue V solution is from 5 to 25 mg/ml.

4. A test paper according to claim 1, wherein the concentration of said Patent Blue V contained in said mixed berberine sulfate/Patent Blue V solution is from 0.2 to 0.5 mg/ml.

5. A test paper according to claim 1, wherein said filter paper has uniform wettability, and is rectangular or circular.

* * * * *